United States Patent
Yoon et al.

(10) Patent No.: US 11,660,053 B2
(45) Date of Patent: May 30, 2023

(54) APPARATUS AND METHOD FOR MONITORING BIO-SIGNAL MEASURING CONDITION, AND APPARATUS AND METHOD FOR MEASURING BIO-INFORMATION

(71) Applicant: SAMSUNG ELECTRONICS CO., LTD., Suwon-si (KR)

(72) Inventors: Seung Keun Yoon, Seoul (KR); Ui Kun Kwon, Hwaseong-si (KR); Dae Geun Jang, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 919 days.

(21) Appl. No.: 16/258,878

(22) Filed: Jan. 28, 2019

(65) Prior Publication Data

US 2019/0313980 A1    Oct. 17, 2019

Related U.S. Application Data

(60) Provisional application No. 62/658,137, filed on Apr. 16, 2018.

(30) Foreign Application Priority Data

Jul. 4, 2018    (KR) .................... 10-2018-0077656

(51) Int. Cl.
    *A61B 5/00*    (2006.01)
    *A61B 5/0205*    (2006.01)
    (Continued)

(52) U.S. Cl.
    CPC .......... *A61B 5/7282* (2013.01); *A61B 5/0006* (2013.01); *A61B 5/0205* (2013.01);
    (Continued)

(58) Field of Classification Search
    CPC ... A61B 5/7282; A61B 5/0006; A61B 5/0205; A61B 5/02416; A61B 5/681; A61B 5/7207; A61B 5/7235
    See application file for complete search history.

(56) References Cited

U.S. PATENT DOCUMENTS

| | | |
|---|---|---|
| 7,194,293 B2 | 3/2007 | Baker, Jr. |
| 7,613,486 B2 | 11/2009 | Yeo et al. |

(Continued)

FOREIGN PATENT DOCUMENTS

| | | | | |
|---|---|---|---|---|
| EP | 0968681 A1 | * | 1/2000 | ........... A61B 5/6814 |
| EP | 1393673 A1 | * | 3/2004 | ............... A61B 5/35 |

(Continued)

OTHER PUBLICATIONS

Lian Krivoshei, Stefan Weber, Thilo Burkard, Anna Maseli, Noe Brasier, Michael Kühne, David Conen, Thomas Huebner, Andrea Seeck, Jens Eckstein, Smart detection of atrial fibrillation, EP Europace, vol. 19, Issue 5, May 2017, pp. 753-757, https://doi.org/10.1093/europace/euw125 (Year: 2017).*

(Continued)

*Primary Examiner* — Joshua B Blanchette
(74) *Attorney, Agent, or Firm* — Sughrue Mion, PLLC

(57) ABSTRACT

An apparatus and a method for monitoring a bio-signal measuring condition are disclosed. The apparatus includes a bio-signal receiver configured to receive a bio-signal that is measured from a user, and a processor configured to extract any one or any combination of a waveform feature, a period feature, and an amplitude feature, from the received bio-signal, determine whether the extracted any one or any combination of the waveform feature, the period feature, and the amplitude feature are normal, using at least one predetermined determination reference corresponding to the extracted any one or any combination of the waveform feature, the period feature, and the amplitude features, and (Continued)

monitor a measuring condition of the received bio-signal, based on whether the extracted any one or any combination of the waveform feature, the period feature, and the amplitude feature are determined to be normal.

32 Claims, 14 Drawing Sheets

(51) Int. Cl.
  *G16H 50/20* (2018.01)
  *A61B 5/024* (2006.01)
(52) U.S. Cl.
  CPC ............ *A61B 5/681* (2013.01); *A61B 5/7207* (2013.01); *A61B 5/7235* (2013.01); *A61B 5/0015* (2013.01); *A61B 5/02416* (2013.01); *G16H 50/20* (2018.01)

(56) References Cited

U.S. PATENT DOCUMENTS

| | | | |
|---|---|---|---|
| 8,603,001 | B2 | 12/2013 | Fujita et al. |
| 9,011,343 | B2 | 4/2015 | Shimizu |
| 9,026,206 | B2 | 5/2015 | Krause et al. |
| 9,833,185 | B2 | 12/2017 | Leininger et al. |
| 10,024,816 | B2 | 7/2018 | Kim et al. |
| 2004/0220483 | A1 | 11/2004 | Yeo et al. |
| 2014/0299487 | A1 | 10/2014 | Kim et al. |
| 2016/0113589 | A1 | 4/2016 | Yoon |
| 2017/0209055 | A1 | 7/2017 | Pantelopoulos et al. |
| 2017/0268923 | A1* | 9/2017 | Yamada ............... A61B 5/1038 |
| 2018/0000424 | A1 | 1/2018 | Demirtas et al. |

FOREIGN PATENT DOCUMENTS

| | | |
|---|---|---|
| JP | 2010-46236 A | 3/2010 |
| JP | 2015-66401 A | 4/2015 |
| JP | 2016-96989 A | 5/2016 |
| KR | 10-0519758 B1 | 10/2005 |
| KR | 10-2012-0108575 A | 10/2012 |
| KR | 10-2016-0047838 A | 5/2016 |
| KR | 10-1779505 B1 | 9/2017 |
| WO | 2013/069895 A1 | 5/2013 |

OTHER PUBLICATIONS

Communication dated Aug. 16, 2019 issued by the European Intellectual Property Office in counterpart European Application No. 19161833.9.

* cited by examiner

APPARATUS AND METHOD FOR MONITORING BIO-SIGNAL MEASURING CONDITION, AND APPARATUS AND METHOD FOR MEASURING BIO-INFORMATION

CROSS-REFERENCE TO RELATED APPLICATIONS

This application claims priority from Korean Patent Application No. 10-2018-0077656, filed on Jul. 4, 2018, in the Korean Intellectual Property Office, and U.S. Provisional Patent Application No. 62/658,137, filed on Apr. 16, 2018, in the U.S. Patent and Trademark Office, the disclosures of which are incorporated herein by reference in their entities.

BACKGROUND

1. Field

Apparatuses and methods consistent with embodiments relate to an apparatus and a method for monitoring bio-signal measuring conditions, and more particularly to technology for monitoring measuring conditions by using measurement results of bio-signals.

2. Description of the Related Art

Recently, with the aging population, soaring medical costs, and a lack of medical personnel for specialized medical services, research is being actively conducted on IT-medical convergence technologies, in which IT technology and medical technology are combined. Particularly, monitoring of the health condition of the human body is not limited to places such as hospitals, but is expanding to mobile healthcare fields that may monitor a user's health state anywhere and anytime in daily life at home or office. Examples of bio-signals, which indicate the health condition of individuals, may include an electrocardiography (ECG) signal, a photoplethysmogram (PPG) signal, an electromyography (EMG) signal, and the like, and various bio-signal sensors are being developed to measure these signals in daily life. However, when bio-signals are detected using these bio-signal sensors, the measured bio-signals may be inaccurate due to circumstances such as a wearing state of a bio-information measuring apparatus, a user's posture, or the like.

SUMMARY

According to embodiments, there is provided an apparatus for monitoring a bio-signal measuring condition, the apparatus including a bio-signal receiver configured to receive a bio-signal that is measured from a user, and a processor configured to extract any one or any combination of a waveform feature, a period feature, and an amplitude feature, from the received bio-signal, determine whether the extracted any one or any combination of the waveform feature, the period feature, and the amplitude feature are normal, using at least one predetermined determination reference corresponding to the extracted any one or any combination of the waveform feature, the period feature, and the amplitude features, and monitor a measuring condition of the received bio-signal, based on whether the extracted any one or any combination of the waveform feature, the period feature, and the amplitude feature are determined to be normal.

The processor may be further configured to determine whether the extracted waveform feature is normal, using a waveform self-reference that is individualized for the user.

The waveform self-reference may include any one or any combination of a reference time interval, a number of comparison samples, an order of differentiation, and a failure condition.

The processor may be further configured to extract a waveform of a current time interval, from the received bio-signal, obtain a first waveform and a second waveform, from the extracted waveform of the current time interval and a waveform of the reference time interval, based on the order of differentiation, compare the obtained first waveform and the obtained second waveform, and based on a result of the obtained first waveform being compared with the obtained second waveform satisfying the failure condition, determine that the extracted waveform feature is abnormal.

The processor may further include a buffer configured to store data of the waveform of the reference time interval of the bio-signal.

The processor may be further configured to, based on the waveform of the current time interval satisfying a predetermined update reference, update the stored data of the waveform of the reference time interval, using data of the waveform of the current time interval.

The failure condition may include any one or any combination of a minimum threshold of similarity between waveforms, a number of times of successive failures to reach the minimum threshold, a start point of a similarity comparison between waveforms, and a total beat count for calculating an average similarity value.

The processor may be further configured to calculate a similarity between the obtained first waveform and the obtained second waveform, and based on the calculated similarity being lower than the minimum threshold, determine that the extracted waveform feature is abnormal.

The processor may be further configured to, based on the calculated similarity between the obtained first waveform and the obtained second waveform being lower than the minimum threshold, and the number of times of the successive failures to reach the minimum threshold satisfying a predetermined number of times, determine that the extracted waveform feature is abnormal.

The similarity between the waveforms may include any one or any combination of a correlation coefficient, an average value, and a sum total of comparison samples of the first waveform and the second waveform.

The processor may be further configured to determine whether the extracted period feature is normal, using either one or both of a period self-reference that is individualized for the user and a period general reference for bio-information to be measured using the bio-signal.

The extracted period feature may include either one or both of a current period of the received bio-signal and an average period of the received bio-signal during a predetermined period of time.

The processor may be further configured to determine whether the extracted amplitude feature is normal, using an amplitude self-reference that is individualized for the user.

The processor may be further configured to output either one or both of a reliability of the measuring condition of the bio-signal and information of the measuring condition, based on whether the extracted any one or any combination of the waveform feature, the period feature, and the amplitude feature are determined to be normal in parallel or in series according to predetermined priorities of each of the extracted any one or any combination of the waveform feature, the period feature, and the amplitude feature.

The predetermined priorities may be determined based on any one or any combination of an examination position, types of bio-signals, types of bio-information to be measured, and a computing performance of a bio-information measuring apparatus.

The processor may be further configured to based on the extracted amplitude feature being determined to be normal, while the extracted period feature and the extracted waveform feature are determined to be abnormal, determine the measuring condition to be a motion noise condition, based on the extracted period feature being determined to be normal, while the extracted amplitude feature and the extracted waveform feature are determined to be abnormal, determine the measuring condition to be an ambient light noise condition, based on the extracted waveform feature being determined to be normal, while the extracted period feature and the extracted amplitude feature are determined to be abnormal, determine the measuring condition to be a condition of not measuring the bio-signal, based on the extracted period feature being determined to be abnormal, while the extracted amplitude feature and the extracted waveform feature are determined to be normal, determine the measuring condition to be a condition of cardiac arrhythmia, based on the extracted amplitude feature being determined to be abnormal, while the extracted period feature and the extracted waveform feature are determined to be normal, determine the measuring condition to be an inadequate contact pressure condition, based on the extracted waveform feature being determined to be abnormal, while the extracted period feature and the extracted amplitude feature are determined to be normal, determine the measuring condition to be a contact failure condition, and based on the extracted period feature, the extracted amplitude feature, and the extracted waveform features being determined to be normal, determine the measuring condition to be a normal measuring condition.

According to embodiments, there is provided a method for monitoring a bio-signal measuring condition, the method including receiving a bio-signal that is measured from a user, extracting any one or any combination of a waveform feature, a period feature, and an amplitude feature, from the received bio-signal, determining whether the extracted any one or any combination of the waveform feature, the period feature, and the amplitude feature are normal, using a predetermined determination reference corresponding to the extracted any one or any combination of the waveform feature, the period feature, and the amplitude features, and monitoring a measuring condition of the received bio-signal, based on whether the extracted any one or any combination of the waveform feature, the period feature, and the amplitude feature are determined to be normal.

The determining whether the extracted any one or any combination of the waveform feature, the period feature, and the amplitude feature are normal may include determining whether the extracted waveform feature is normal, using a waveform self-reference that is individualized for the user.

The determining whether the extracted waveform feature is normal may include extracting a waveform of a current time interval, from the received bio-signal, obtaining a first waveform and a second waveform, from the extracted waveform of the current time interval and a waveform of a reference time interval, based on an order of differentiation, comparing the obtained first waveform and the obtained second waveform, and based on a result of the obtained first waveform being compared with the obtained second waveform satisfying a failure condition, determining that the extracted waveform feature is abnormal.

The comparing the obtained first waveform and the obtained second waveform may include calculating a similarity between the obtained first waveform and the obtained second waveform, and the determining that the extracted waveform feature is abnormal may include, based on the calculated similarity being lower than a minimum threshold of similarity between waveforms, determining that the extracted waveform feature is abnormal.

The determining whether the extracted any one or any combination of the waveform feature, the period feature, and the amplitude feature are normal may include determining whether the extracted period feature is normal, using either one or both of a period self-reference that is individualized for the user and a period general reference for bio-information to be measured using the bio-signal.

The determining whether the extracted any one or any combination of the waveform feature, the period feature, and the amplitude feature are normal may include determining whether the extracted amplitude feature is normal, using an amplitude self-reference that is individualized for the user.

The monitoring the measuring condition of the received bio-signal may include outputting either one or both of a reliability of the measuring condition of the bio-signal and information of the measuring condition, based on whether the extracted any one or any combination of the waveform feature, the period feature, and the amplitude feature are determined to be normal in parallel or in series according to predetermined priorities of each of the extracted any one or any combination of the waveform feature, the period feature, and the amplitude feature.

According to embodiments, there is provided an apparatus for measuring bio-information, the apparatus including a bio-signal measurer configured to measure a bio-signal by emitting a first light onto an object and receiving a second light that is reflected from the object on to which the first light is emitted, a processor configured to extract one or more features, from the measured bio-signal, monitor a measuring condition of the measured bio-signal, using at least one predetermined determination reference corresponding to the extracted one or more features, and perform a pre-defined operation, based on the monitored measuring condition, and an output part configured to output a processing result of the processor, on a display.

The bio-signal measurer may include one or more light sources configured to emit the first light onto the object, and one or more detectors configured to receive the second light reflected from the object.

The processor may be further configured to determine whether the extracted one or more features are normal, using either one or both of a self-reference and a general reference that are included in the at least one predetermined determination reference, and output information of the measuring condition, based on whether the extracted one or more features are determined to be normal.

The processor may be further configured to control the bio-signal measurer to stop and start the measuring of the bio-signal, based on the output information of the measuring condition, and measure the bio-information, using the measured bio-signal, based on the output information of the measuring condition.

The bio-information may include any one or any combination of a heart rate, a cardiac arrhythmia, a blood pressure, a vascular age, an arterial stiffness, an aortic pressure waveform, a vascular compliance, a stress index, and a degree of fatigue.

The apparatus may further include a storage part configured to store any one or any combination of the at least one predetermined determination reference, the measured bio-signal, information on whether each of the extracted one or more features is determined to be normal, the monitored measuring condition, and the measured bio-information.

The apparatus may further include a communicator configured to transmit and receive, to and from an external device, the at least one predetermined determination reference, the measured bio-signal, information on whether each of the extracted one or more features is determined to be normal, the monitored measuring condition, and the measured bio-information.

According to embodiments, there is provided a method for measuring bio-information, the method including measuring a bio-signal by emitting a first light onto an object and receiving a second light that is reflected from the object on to which the first light is emitted, extracting one or more features, from the measured bio-signal, monitoring a measuring condition of the measured bio-signal, using at least one predetermined determination reference corresponding to the extracted one or more features, and performing a pre-defined operation, based on the monitored measuring condition.

The monitoring the measuring condition of the bio-signal may include determining whether the extracted one or more features are normal, using either one or both of a self-reference and a general reference that are included in the at least one predetermined determination reference, and based on whether the extracted one or more features are determined to be normal, outputting information of the measuring condition including any one or any combination of a motion noise condition, an ambient light noise condition, a condition of not measuring the bio-signal, a condition of cardiac arrhythmia, an inadequate contact pressure condition, a contact failure condition, and a normal measuring condition.

The performing the pre-defined operation may include, based on the output information of the measuring condition, controlling to stop and start the measuring of the bio-signal, and measuring bio-information, using the measured bio-signal.

The method may further include outputting a result of the measuring the bio-information.

According to embodiments, there is provided an apparatus for monitoring a bio-signal measuring condition, the apparatus includes a bio-signal receiver configured to receive a bio-signal that is measured from a user, and a processor configured to extract a waveform, a period, and an amplitude, from the received bio-signal, determine whether the extracted waveform is normal by comparing the extracted waveform to a reference waveform, determine whether the extracted amplitude is normal by comparing the extracted amplitude to a reference amplitude, determine whether the extracted period is normal by comparing the extracted period to a reference period, based on the extracted amplitude being determined to be abnormal, control to output any one or any combination of an inadequate contact pressure condition, an ambient light noise condition, and a condition of not measuring the bio-signal, based on one of the extracted period and the extracted waveform being determined to be abnormal, control to output any one or any combination of a motion noise condition, a condition of cardiac arrhythmia, and a contact failure condition, and based on the extracted amplitude, the extracted period, and the extracted waveform being determined to be normal, control to output a normal measuring condition.

The determining whether the extracted waveform is normal may include determining that the extracted waveform is normal, based on a similarity of the extracted waveform and the reference waveform being greater than a threshold, the determining whether the extracted amplitude is normal may include determining that the extracted amplitude is normal, based on a first difference between the extracted amplitude and the reference amplitude being within a first range, and the determining whether the extracted period is normal may include determining that the extracted period is normal, based on a second difference between the extracted period and the reference period being within a second range.

DETAILED DESCRIPTION

Figure 1:
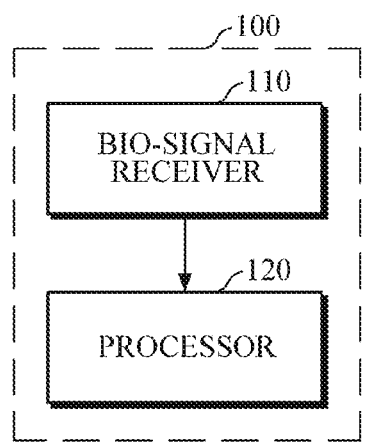
FIG. 1 is a block diagram illustrating an apparatus for monitoring a bio-signal measuring condition according to an embodiment of the disclosure.

Details of embodiments are included in the following detailed description and drawings. Advantages and features of the embodiments, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., may be understood as a unit that performs at least one function or operation and that may be embodied as hardware, software, or a combination thereof.

Hereinafter, embodiments of an apparatus and method for extracting features for detecting bio-information, an apparatus for detecting bio-information, and a wearable device will be described in detail with reference to the accompanying drawings.

FIG. 1 is a block diagram illustrating an apparatus for monitoring a bio-signal measuring condition according to an embodiment of the disclosure.

Referring to FIG. 1, an apparatus 100 for monitoring a bio-signal measuring condition includes a bio-signal receiver 110 and a processor 120.

The bio-signal receiver 110 may receive a bio-signal of a user. In this case, the bio-signal may be an electrocardiography (ECG) signal, a photoplethysmogram (PPG) signal, an electromyography (EMG) signal, and the like, but the bio-signal is not limited thereto.

For example, the bio-signal receiver 110 may include a bio-signal measuring sensor for measuring a bio-signal from a user. In another example, the bio-signal receiver 110 may be connected to the bio-signal measuring sensor through wired or wireless communication to receive a user's bio-signal from the bio-signal measuring sensor. In yet another example, the bio-signal receiver 110 may be connected to an external device through wired or wireless communication to receive bio-signal data from the external device. In this case, the external device may be an information processing device such as a wearable device, a smartphone, a tablet PC, a desktop computer, a laptop computer, and the like, and may be an apparatus for processing and managing bio-signal data.

Once a bio-signal of a user is received, the processor 120 may monitor a measuring condition of the bio-signal, which is measured from the user, by using the received bio-signal. For example, the processor 120 may monitor a measuring condition of the bio-signal based on a predetermined determination reference that may include a general reference, which may be applied according to bio-signals and bio-information to be measured, and a self-reference individualized for each user.

For example, bio-signals, which are measured repeatedly, have features that are repeated similarly for a predetermined period of time. Examples of the features include a period, an amplitude, and the like, of which values do not converge or diverge; and some other features of the bio-signals, such as a bio-signal waveform and the like, are repeated similarly for a predetermined period of time. In this case, if bio-information to be measured is a heart rate, there may be a general reference for a period, for example, a heart rate ranging from 30 bpm to 180 bpm, which may be determined to be normal. As described above, there may be a general reference that may be applied to most people according to types and characteristics of bio-signals, and the like. However, there may be no such general reference depending on bio-signals in some cases, in which a self-reference may be pre-defined based on bio-signals and individual characteristics of users according to embodiments of the disclosure.

Hereinafter, referring to FIGS. 2 and 3, various embodiments of a configuration of the processor 120 will be described in further detail. However, the processor 120 is not limited to the embodiments and may be modified in various manners.

Figure 2:
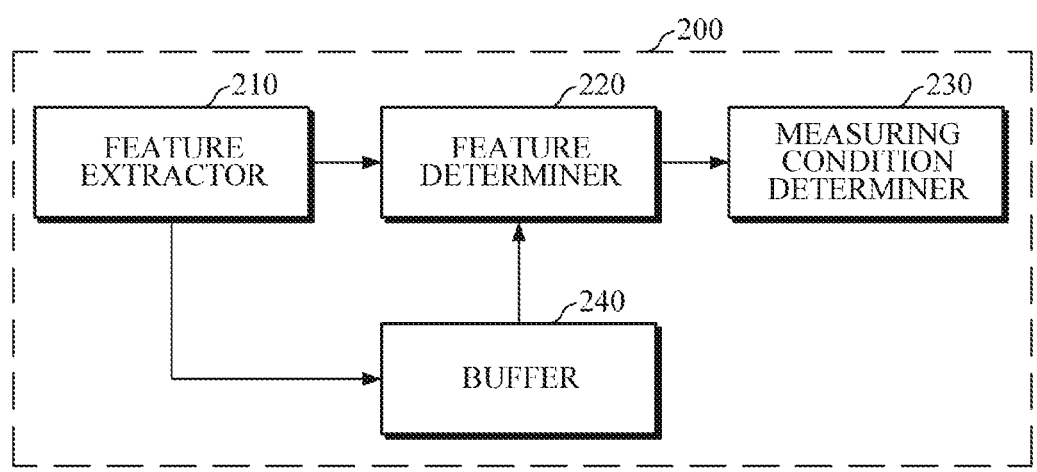
FIG. 2 is a diagram illustrating an example of a configuration of a processor of the apparatus for monitoring a bio-signal measuring condition of FIG. 1.

FIG. 2 is a diagram illustrating an example of a configuration of a processor of the apparatus for monitoring a bio-signal measuring condition of FIG. 1. FIG. 3 is a diagram illustrating another example of a configuration of a processor of the apparatus for monitoring a measuring condition of FIG. 1. FIGS. 4A, 4B and 4C are diagrams explaining an example of monitoring a measuring condition of a bio-signal.

Referring to FIG. 2, a processor 200 includes a feature extractor 210, a feature determiner 220, a measuring condition determiner 230, and a buffer 240.

Once a bio-signal is received, the feature extractor 210 may extract one or more features from the received bio-signal. In this case, the features may include an amplitude feature, a period feature, a waveform feature, and the like, but are not limited thereto. Once a bio-signal is received, the feature extractor 210 may remove noise by filtering the received bio-signal as needed. Further, the feature extractor 210 may perform normalization to compare the extracted features with a determination reference.

The feature extractor 210 may store the currently extracted features in the buffer 240 to use the features as a reference for determining whether features extracted at a subsequent time are normal.

For example, the feature extractor 210 may extract, as an amplitude feature, a difference between a maximum value and a minimum value of a bio-signal during a time or a filtered bio-signal. Further, the feature extractor 210 may store the currently extracted features in the buffer 240 to use the features as a reference for determining whether features extracted at a subsequent time are normal.

FIG. 4A illustrates a bio-signal measured from a user or a filtered bio-signal, e.g., a PPG signal. As illustrated in FIG. 4A, the feature extractor 210 may extract, as an amplitude feature, an amplitude value at a maximum amplitude point Amax, which is a difference between a maximum amplitude point Amax and an amplitude minimum point Amin during a time period between time indices 0 and 140. Alternatively, the feature extractor 210 may perform secondary differentiation of a bio-signal to obtain a secondary differential signal, may obtain a time of a local minimum point, at which an amplitude is at a minimum during a period of time in the obtained secondary differential signal, from the obtained secondary differential signal, and may extract an amplitude value, corresponding to the time of the local minimum point, as an amplitude feature. However, the features are not limited thereto.

For example, the feature extractor 210 may extract a current period of a bio-signal, and may store the extracted current period in the buffer 240. As illustrated in FIG. 4A, the feature extractor 210 may extract an interval between a point 0, where an amplitude value is zero (0) for the first time, and a point 140 where an amplitude value is zero (0) for a subsequent second time, as a current period, but is not limited thereto.

Further, the feature extractor 210 may extract an average period of a bio-signal, and may store the extracted average period in the buffer 240. The feature extractor 210 may obtain a total number of times that an amplitude value is zero (0) during a time, and may calculate an average period based on the obtained total number of times. For example, the feature extractor 210 may calculate, as the average period, a time interval by dividing the time by the total number of times.

In addition, the feature extractor 210 may extract a waveform feature from a received bio-signal or a filtered bio-signal, and may store the extracted waveform feature in the buffer 240 to use the currently extracted waveform feature as a reference for determining whether features extracted at a subsequent time are normal.

For example, the feature extractor 210 may continuously extract m number of values, which is set as a number of comparison samples, in a current time interval, and may use the extracted values as a waveform feature. In this case, the extracted values may be an n-th order differential value or integral value, and the like. However, the values are not limited thereto, and may be various values that may be extracted from a bio-signal. In this case, the number of samples may be maintained at a constant value. Further, a length of a time interval, in which the waveform feature is extracted, may be preset to a random value. In addition, as described above, a period, which is extracted in the process of extracting a period feature, may be set as a length of a time interval. In the case in which each period, e.g., a previous period and a current period, have different lengths of time, each period may be normalized so that the lengths of time intervals may be equal to each other. In this manner, the number of signal samples extracted in each period may be equal to each other. Further, the m number of samples to be extracted may be pre-defined in a waveform self-reference.

Referring again to FIG. 2, once the feature extractor 210 extracts each of the features, the feature determiner 220 may determine whether each feature is normal by using a general reference and/or a self-reference that are defined for each of the features. In this case, the general reference and/or the self-reference may be applied in series or in parallel. By referring to the buffer 240, the feature determiner 220 may obtain information associated with the general reference or the self-reference defined for each of the features, and may determine whether each feature is normal.

Once an amplitude feature is extracted from a bio-signal at a current time, the feature determiner 220 may determine whether the extracted amplitude feature is normal by using the amplitude self-reference. In this case, the amplitude self-reference may be pre-defined to determine that the amplitude feature is abnormal if a difference between an amplitude feature value measured at a reference time and an amplitude feature value measured at the current time falls outside a predetermined range, or if the amplitude feature value at the current time falls outside a predetermined percentage of the amplitude feature value at the reference time. However, such self-reference may be set variously according to the features of bio-signals, types of bio-information, individual characteristics of users, e.g., a health state, specificity of an examination portion, and the like.

However, references are not limited thereto, and there may be an amplitude general reference that may be applied according to the types of bio-signals, the types of bio-information to be extracted, the features of the extracted bio-signal, and the like. In this case, the feature determiner 220 may determine whether an amplitude feature is normal by applying the amplitude general reference alone or in combination with the amplitude self-reference.

Once a current period feature at the current time and/or an average period feature are extracted, the feature determiner 220 may determine whether the current period feature and/or the average period feature are normal by applying a period general reference and/or a period self-reference. In this case, the period general reference is a reference applied according to bio-signals and bio-information. For example, in the case of measuring a heart rate by using a PPG signal, there may be a general reference to determine that a heart rate ranging from 30 bpm to 180 bpm is normal.

In addition, the period self-reference is preset by considering individual characteristics of a user, e.g., a user's gender, health state, age, examination position, characteristics of the examination position, and the like. The period self-reference may be preset to determine that a period feature is abnormal if a difference between a current period value at the current time or a period value at the reference time falls outside a predetermined range, or if the current period falls outside a predetermined percentage of the period at the reference time. In this case, the reference time may refer to a preceding period extracted at a preceding time. For example, in the case in which a preceding period is 0.84 seconds (approximately 71 bpm), the period self-reference may define a range of 0.67 sec. to 1.01 sec., which are in a range of 20% of 0.84 sec., to be a normal range; and if the extracted current period falls outside the range of 0.67 sec. to 1.01 sec., the feature determiner 220 may determine the period feature is abnormal.

Once a waveform feature in the current time interval is extracted, the feature determiner 220 may obtain information associated with the waveform self-reference by referring to the buffer 240, and may determine whether the extracted waveform feature is normal by using the obtained information associated the waveform self-reference.

The waveform self-reference may include a reference time interval, the number of comparison samples, the order of differentiation or integration, failure conditions, and the like. In this case, the reference time interval may be a preceding time interval in which waveform is extracted at a preceding time. Further, the time interval may be divided in units of periods. Hereinafter, for convenience of explanation, the reference time interval and the current time interval will be described as the reference period and the current period, but are not limited thereto.

In addition, the number of comparison samples is the number of samples to be extracted, and may be pre-defined based on a sampling rate, a buffer size, and the like. For example, in the case in which a sampling rate of a bio-signal is 250 Hz, the number of samples to be extracted may be set to 50, which corresponds to 20% of the sampling rate. Further, there may be one or more failure conditions, and in the case in which there are two or more failure conditions, the conditions may be set to determine that a waveform feature is abnormal if some or all pre-defined conditions are satisfied. For example, the failure conditions may include a minimum threshold of similarity, a number of times of successive failures to reach the minimum threshold, a start point of similarity comparison, a total beat count for an average similarity value, and the like, but are not limited thereto.

For example, once a waveform feature of the current period is extracted, the feature determiner 220 may obtain a waveform feature of the reference period by referring to the buffer 240, and may calculate similarity between the waveform feature of the current period and the waveform feature of the reference period. In this case, the extracted two waveforms are m number of continuous values, such that a correlation coefficient $r_{x,y}$ may be calculated as similarity, as represented by the following Equation 1. In this case, outliers may be excluded from among the m number of waveform features.

$$r_{x,y} = \frac{\text{cov}(X, Y)}{\sigma_x \sigma_y} = \frac{E[(X - \mu_x)(Y - \mu_y)]}{\sigma_x \sigma_y} \quad \text{[Equation 1]}$$

$$E[(X - \mu_x)(Y - \mu_y)] = \frac{\sum_{i=1}^{m}(X_i - \mu_x)(Y_i - \mu_y)}{m}$$

Herein, $\mu_x$ denotes the mean of population X, $\mu_y$ denotes the mean of population Y, $\sigma_x$ denotes the standard deviation of the population X, $\sigma_y$ denotes the standard deviation of the population Y, and m denotes the number of individuals in the population. The correlation coefficient is in a range of $-1 \leq r_{x,y} \leq 1$, and as the value of the correlation coefficient is closer to 1, the two waveforms are similar to each other. However, calculation of similarity is not limited thereto, and statistical values, such as an average value, a sum total, and the like, of a plurality of samples of the waveform features may be calculated as similarity.

In the case in which the calculated similarity falls outside a minimum threshold among the waveform self-reference, the feature determiner 220 may determine that the waveform feature is abnormal. Alternatively, in the case in which the waveform feature of the current period is abnormal, and a determination result, obtained by continuously determining features of the previous periods, satisfies a number of times of successive failures to reach the minimum threshold, the feature determine 220 may finally determine that the waveform feature is abnormal. The feature determiner 220 may calculate similarity by using values obtained after the start point of similarity comparison.

Based on information on the order of differentiation/integration among the waveform self-reference information, the feature determiner 220 may obtain a first waveform and a second waveform by performing differentiation/integration of a waveform of the current period and a waveform of the reference period based on a corresponding order of differentiation/integration. The order of differentiation/integration, which is set to '0', may indicate the extracted waveform features themselves. The feature determiner 220 may calculate similarity by comparing the obtained first waveform and second waveform, and may determine whether the waveform feature of the current period is normal by using the calculated similarity as described above.

Referring to FIG. 4B, an example is illustrated in which in the case in which similarity between the current waveform and the reference waveform, which are extracted from a PPG signal, is lower than or equal to 0.7 that is a value set as a minimum threshold, it is determined that the waveform feature is abnormal and '0' is input into the buffer 240; and in the case in which the similarity is greater than 0.7, it is determined that the waveform feature is normal and '1' is input into the buffer 240. As illustrated in FIG. 4B, it can be seen that a result of comparison at the current time T7 between similarity and the minimum threshold is determined to be normal. In the case in which the number of times of successive failures to reach the minimum threshold is set to '4', it is determined that a result of comparison at time T4 is abnormal (0), and there are four consecutive times of determining abnormal results, including the result at T4, such that a final determination result may indicate that the waveform feature obtained at T4 is abnormal.

Referring to FIG. 4C, an example is illustrated in which in the case in which similarity between a current waveform and a reference waveform, which are obtained from a secondary differential signal by performing secondary differentiation of the PPG signal of FIG. 4B, is lower than or equal to 0.6, which is a value set as a minimum threshold, it is determined that the waveform feature is abnormal and '0' is input into the buffer 240; and in the case in which the similarity is greater than 0.6, it is determined that the waveform feature is normal and '1' is input into the buffer 240.

Referring again to FIG. 2, by comprehensively considering the determination results of each of the features, the monitoring condition determiner 230 may monitor a final measuring condition of a bio-signal measured from a user, and may output one or more of reliability of a bio-signal measuring condition and measuring condition information as a monitoring result. In this case, the measuring condition information may include any one or any combination of a motion noise condition, an ambient light noise condition, a condition of not measuring a bio-signal, a condition of cardiac arrhythmia, an inadequate contact pressure condition, a contact failure condition, and a normal measuring condition. By considering the determination results of each of the features in parallel, the measuring condition determiner 230 may output the reliability and/or the measuring condition information. Alternatively, by considering the determination results of each of the features in series according to predetermined priorities of the features, the measuring condition determiner 230 may output a final monitoring result.

For example, in response to determination that an amplitude feature is normal, while period and waveform features are abnormal, the measuring condition determiner 230 may determine a measuring condition to be a motion noise condition. Alternatively, in response to determination that the period feature is normal, while the amplitude and waveform features are abnormal, the measuring condition determiner 230 may determine a measuring condition to be a light noise condition in which there is much ambient light noise. Further, in response to determination that the waveform feature is normal, while the period and amplitude features are abnormal, the measuring condition determiner 230 may determine a measuring condition to be a condition of not measuring a bio-signal in which a bio-signal is not measured. In addition, in response to determination that the period feature is abnormal, while the amplitude and waveform features are normal, the measuring condition determiner 230 may determine a measuring condition to be a condition of cardiac arrhythmia. Moreover, in response to determination that the amplitude feature is abnormal, while the period and waveform features are normal, the measuring condition determiner 230 may determine a measuring condition to be an inadequate contact pressure condition. Furthermore, in response to determination that the waveform feature is abnormal, while the period and amplitude features are normal, the measuring condition determiner 230 may determine a measuring condition to be a contact failure condition in which contact is failed or there is vibration in a contact portion. In addition, in response to determination that the period, amplitude, and waveform features are all normal, the measuring condition determiner 230 may determine a measuring condition to be a normal measuring condition. However, the conditions are examples, and may be combined in various manners.

Figure 3:
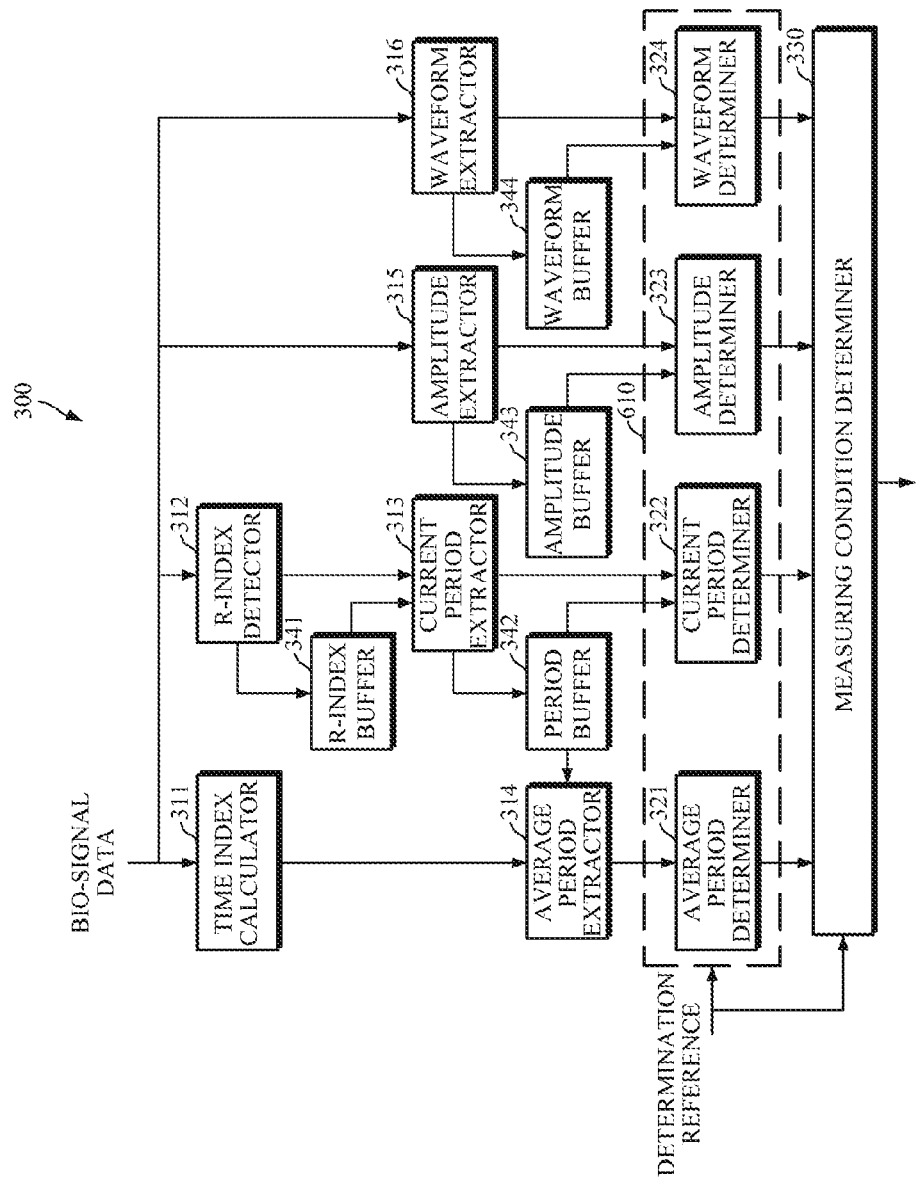
FIG. 3 is a diagram illustrating another example of a configuration of a processor of the apparatus for monitoring a measuring condition of FIG. 1.
Figure 4A:
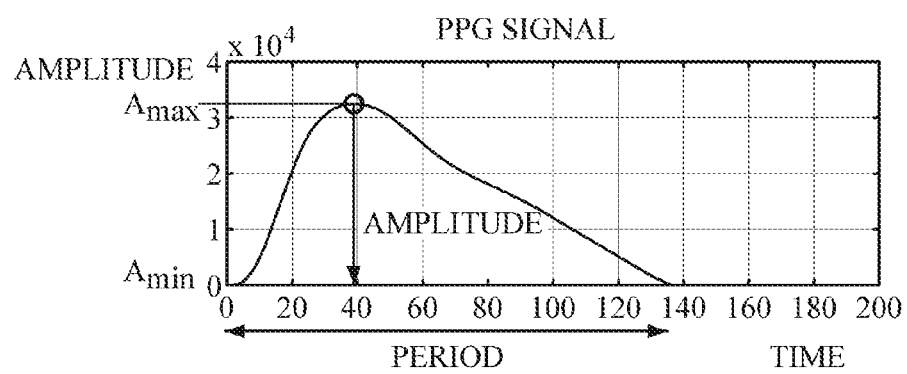
FIGS. 4A, 4B and 4C are diagrams explaining an example of monitoring a measuring condition of a bio-signal.
Figure 4B:
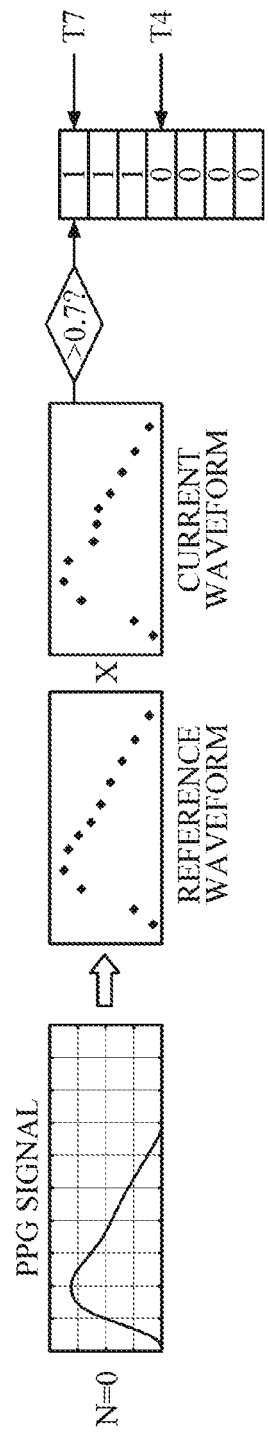
Figure 4C:
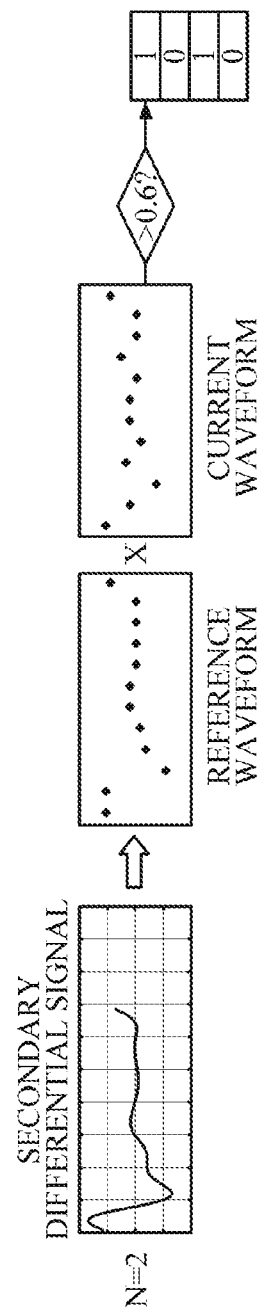

Referring to FIG. 3, a processor 300 includes a time index calculator 311, an R-index detector 312, a current period extractor 313, an average period extractor 314, an amplitude extractor 315, a waveform extractor 316, an average period determiner 321, a current period determiner 322, an amplitude determiner 323, a waveform determiner 324, a measuring condition determiner 330, an R-index buffer 341, a period buffer 342, an amplitude buffer 343, and a waveform buffer 344.

The time index calculator 311 may measure time in response to input of bio-signal data. For example, an input speed of the bio-signal data determined according to a sampling rate and a buffer size, such that time may be measured based on the input speed of the bio-signal data.

The R-index detector 312 may detect an R-peak index from an input bio-signal or a filtered signal from which noise is removed. The R-peak index is a value used as a reference for measuring a period of a bio-signal, and may be a point at which a negative (−) value is changed to a positive (+) value, a point at which a positive (+) value is changed to a negative (−) value, a point of inflection, and the like. Further, upon detecting the R-peak index, the R-index detector 312 may input the detected R-peak index into an R-index buffer 314.

By referring to the R-peak index stored in the R-index buffer 314, the current period extractor 313 may extract a current period. The current period extractor 313 may store the extracted current period value in the period buffer 342 to use the current period value as a reference period for a subsequent time.

The average period extractor 314 may calculate an average period by using period information stored in the period buffer 342 and time values measured by the time index calculator 311. For example, in the case in which during a predetermined time (e.g., 30 minutes) measured by the time index calculator 311, three periods, e.g., 10 min., 8 min., and 12 min., are extracted by the period extractor 313 and stored in the period buffer 342, the average period extractor 314 may calculate an average period of 10 min.

The amplitude extractor 315 may extract amplitude feature values from the input bio-signal or the filtered bio-signal. For example, the amplitude extractor 315 may extract, for example, a difference between a maximum value and a minimum value as an amplitude value during a period of time from the bio-signal or the filtered bio-signal. Further, the extracted amplitude value may be stored in the amplitude buffer 343 to be used as a self-reference for comparing amplitude values at a subsequent time.

The waveform extractor 210 may extract a waveform feature from the received bio-signal or the filtered bio-signal. In this case, the waveform extractor 210 may extract a plurality of samples from the bio-signal itself or a differential signal obtained by differentiating the bio-signal. In this case, the waveform extractor 210 may extract, as the waveform feature, the plurality of samples by using information whether n-th order differentiation is performed and information on the number of comparison samples among the determination reference information. The waveform feature extracted at the current time may be input into the waveform buffer 344 to be used as a self-reference for determining whether a waveform feature at a subsequent time is normal.

The average period determiner 321 may determine whether the average period, extracted by the average period extractor 314, is normal by using a period general reference among the input determination references. The current period determiner 322 may determine whether the current period value, extracted by the current period extractor 313, is normal based on the reference period value stored in the period buffer 342 and the period self-reference among the input determination references.

The amplitude determiner 323 may determine whether the current amplitude value, extracted by the amplitude extractor 315, is normal by applying the reference amplitude value stored in the amplitude buffer 343 and the amplitude self-reference among the input determination references.

The waveform determiner 316 may determine whether a current waveform, extracted by the waveform extractor 316, is normal by applying the reference waveform stored in the waveform buffer 344 and the waveform self-reference among the input determination references. In this case, the waveform determiner 316 may calculate similarity between the reference waveform and the current waveform, and may determine whether the current waveform is normal based on the calculated similarity.

In response to input of determination results of the average period, the current period, and the amplitude and waveform features, the measuring condition determiner 330 may monitor a final measuring condition of a bio-signal measured from a user, by considering the determination results of each of the features in series/in parallel. Information on whether to consider the results in series or in parallel may be predetermined in the input determination references. In the case of consideration in series, priorities of features may be pre-defined.

The measuring condition determiner 330 may output, as a monitoring result, one or more of reliability of a bio-signal monitoring condition and measuring condition information. In this case, the measuring condition information may include any one or any combination of a motion noise condition, an ambient light noise condition, a condition of not measuring a bio-signal, a condition of cardiac arrhythmia, an inadequate contact pressure condition, a contact failure condition, and a normal measuring condition.

For example, in response to determination that the amplitude feature is normal, while the period and waveform features are abnormal, the measuring condition determiner 230 may determine a measuring condition to be a motion noise condition. Alternatively, in response to determination that the period feature is normal, while the amplitude and waveform features are abnormal, the measuring condition determiner 230 may determine a measuring condition to be an ambient light noise condition. Further, in response to determination that the waveform feature is normal, while the period and amplitude features are abnormal, the measuring condition determiner 230 may determine a measuring condition to be a condition of not measuring a bio-signal. In addition, in response to determination that the period feature is abnormal, while the amplitude and waveform features are normal, the measuring condition determiner 230 may determine a measuring condition to be a condition of cardiac arrhythmia. Moreover, in response to determination that the amplitude feature is abnormal, while the period and waveform features are normal, the measuring condition determiner 230 may determine a measuring condition to be an inadequate contact pressure condition. Furthermore, in response to determination that the waveform feature is abnormal, while the period and amplitude features are normal, the measuring condition determiner 230 may determine a measuring condition to be a contact failure condition. In addition, in response to determination that the period, amplitude, and waveform features are all normal, the measuring condition determiner 230 may determine a measuring condition to be a normal measuring condition.

Figure 5:
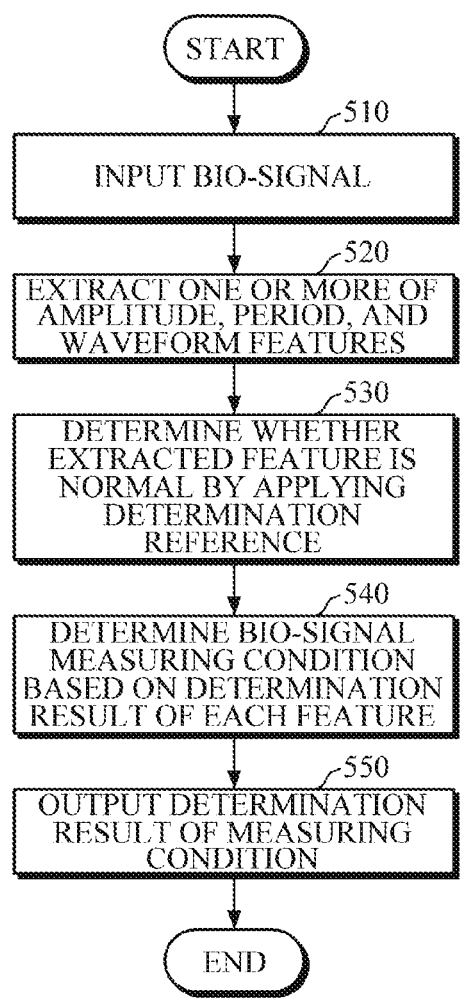
FIG. 5 is a flowchart illustrating a method of monitoring a bio-signal measuring condition according to an embodiment of the disclosure.

FIG. 5 is a flowchart illustrating a method of monitoring a bio-signal measuring condition according to an embodiment of the disclosure.

The method of monitoring a bio-signal measuring condition may be an example of a method performed by the apparatus 100 for monitoring a bio-signal measuring condition of FIG. 1, which is described in detail with reference to FIG. 1 and the following figures, such that the description thereof will be made briefly below.

Referring to FIG. 5, the apparatus 100 for monitoring a bio-signal measuring condition may receive a bio-signal from a user in 510. In this case, the bio-signal may be a PPG signal measured from an examination portion of a user. However, the types of bio-signals are not limited thereto. The bio-signal measured from a user may be received by a bio-signal measuring sensor. Alternatively, the bio-signal may be received from an external device that receives the bio-signal from the bio-signal measuring sensor. In response to input of the bio-signal, the apparatus 100 for monitoring a bio-signal measuring condition may remove noise by filtering the bio-signal as needed.

Then, the apparatus 100 for monitoring a bio-signal measuring condition may extract one or more of amplitude, period, and waveform features from the input bio-signal in 520. As described above, the amplitude feature may be a difference between a maximum value and a minimum value during a period of time. The period feature may include a current period value and an average period value. Further, the apparatus 100 for monitoring a bio-signal measuring condition may extract, as the waveform feature, a value corresponding to a predetermined number of comparison samples during a predetermined time interval, from the bio-signal. In this case, the apparatus 100 for monitoring a bio-signal measuring condition may extract a plurality of samples from the bio-signal or the filtered signal itself, or a differential signal.

Subsequently, the apparatus 100 for monitoring a bio-signal measuring condition may determine whether each of the features, extracted in 520, is normal by applying a predetermined determination reference in 530. In this case, the predetermined determination reference may be set for each of the features, and may include a general reference, which may be applied according to bio-signals and bio-information to be measured, and a self-reference individualized for each user. The apparatus 100 for monitoring a bio-signal measuring condition may determine whether each of the features is normal by applying the general reference or the self-reference in series or in parallel according to each of the features.

Next, the apparatus 100 for monitoring a bio-signal measuring condition may determine a bio-signal measuring condition in 540 based on the determination result in 530. Upon determining in 530 whether the amplitude, period, and waveform features are normal, the apparatus 100 for monitoring a bio-signal measuring condition may determine a bio-signal measuring condition by applying a determination result in parallel or applying a determination result in series according to pre-defined priorities.

Then, the apparatus 100 for monitoring a bio-signal measuring condition may output the determination result of the measuring condition in 550. For example, the apparatus 100 for monitoring a bio-signal measuring condition may output the determination result in a visual manner or in a non-visual manner through voice, vibration, tactile sensation, and the like using an external display module, a haptic module, a speaker module, and the like which are mounted directly in the apparatus 100 or are connected thereto. Alternatively, the apparatus 100 for monitoring a bio-signal measuring condition may transmit the determination result of the measuring condition to an external device that requests the bio-signal measuring condition.

Figure 6:
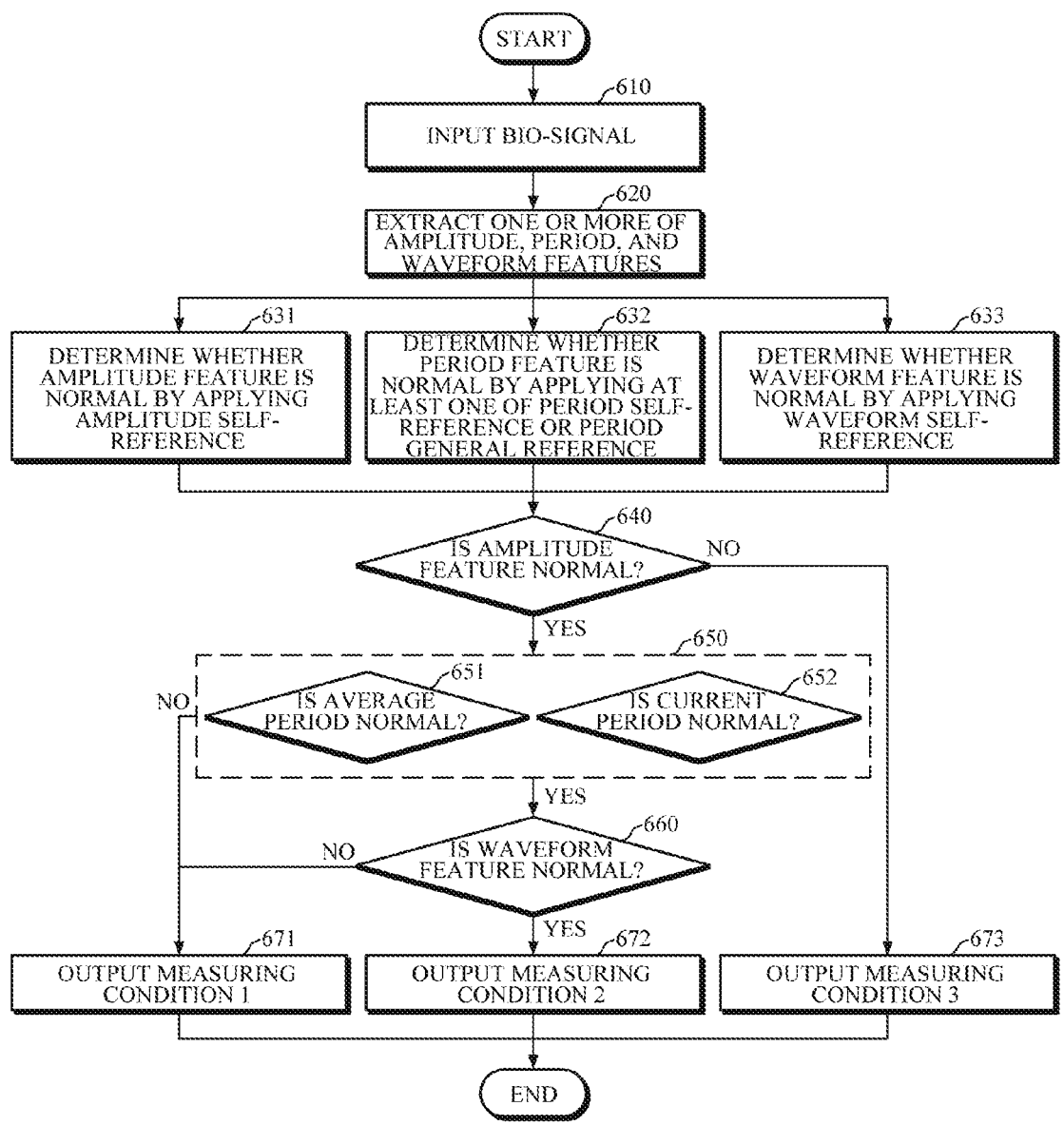
FIG. 6 is a flowchart illustrating a method of monitoring a bio-signal measuring condition according to another embodiment of the disclosure.

FIG. 6 is a flowchart illustrating a method of monitoring a bio-signal measuring condition according to another embodiment of the disclosure. The method of monitoring the bio-signal measuring condition of FIG. 6 may be an example of a method performed by the apparatus 100 for monitoring a bio-signal measuring condition of FIG. 1, which is described in detail with reference to FIG. 1 and the following figures, such that the description thereof will be made briefly below.

The apparatus 100 for monitoring a bio-signal measuring condition may receive a bio-signal from a user in 610. In this case, the bio-signal may be a signal measured from an examination portion of a user, and may be received from a bio-signal measuring sensor or an external device.

Then, the apparatus 100 for monitoring a bio-signal measuring condition may extract one or more of amplitude, period, and waveform features from the input bio-signal in 620.

Subsequently, upon extracting the amplitude feature in 620, the apparatus 100 for monitoring a bio-signal measuring condition may determine whether the amplitude feature is normal by applying an amplitude self-reference in 631. In this case, the amplitude self-reference is pre-defined by considering individual characteristics of a user, and may include a reference time and margin of error information for use in determining abnormal features. In this case, a reference margin of error may be information including a difference between an amplitude feature value measured at the reference time and an amplitude feature value measured at the current time, or range information for determining that an amplitude feature value is abnormal if the amplitude feature value at the current time falls outside a predetermined percentage of an amplitude feature value at the reference time.

Further, upon extracting the period feature in 620, the apparatus 100 for monitoring a bio-signal measuring condition may determine whether the period feature is normal by applying either one or both of the period self-reference and the period general reference in 632. For example, the period feature may include an average period and a current period, and the period general reference may be applied to the average period, and the period self-reference may be applied to the current period. For example, as described above, in the case of measuring a heart rate, when the average period is in a range of 30 bpm to 180 bpm, the apparatus 100 for monitoring a bio-signal measuring condition may determine that the period feature is normal. Further, as described above, in the case in which the current period value falls outside a range of 20% of a preceding period value, the apparatus 100 may determine that the period feature is abnormal.

In addition, upon extracting the waveform feature in 620, the apparatus 100 for monitoring a bio-signal measuring condition may determine whether the extracted waveform feature is normal by applying the waveform self-reference in 633. The waveform self-reference may include a reference time interval, the number of comparison samples, the order of differentiation/integration, failure conditions, and the like. In this case, the failure conditions may be defined to determine that the waveform feature is abnormal in the case in which similarity between two waveforms falls outside a minimum threshold. In this case, the apparatus 100 for monitoring a bio-signal measuring condition may calculate similarity between the waveform of the reference time interval and the waveform of the current time interval, or similarity between two differentiated waveforms obtained by differentiating the two waveforms, and may determine whether the waveform feature is normal by comparing the calculated similarity with the minimum threshold.

The operations 631 to 633 are not necessarily required to be performed in sequential order, but may be performed concurrently or sequentially.

Then, the apparatus 100 may confirm whether a determination result of the amplitude feature is normal or abnormal in 640. Upon confirming that the determination result is abnormal, the apparatus 100 for monitoring a bio-signal measuring condition may output 'measuring condition 3' as a final determination result of a bio-signal measuring condition in 673. In this case, the 'measuring condition 3' may indicate an inadequate contact pressure condition, an ambient light noise condition or a condition of not measuring a bio-signal, but are not limited thereto. For example, FIG. 6 illustrates only an example in which in response to determination that the amplitude feature is abnormal in 640, the process proceeds directly to the operation 673; however, even when the amplitude feature is abnormal, the apparatus 100 for monitoring a bio-signal measuring condition may further consider a result of determination whether the period feature and the waveform feature are normal; and based on the result, the definition of 'measuring condition 3' may be modified in various manners.

Subsequently, upon confirming that the determination result is normal in 640, the apparatus 100 for monitoring a bio-signal measuring condition may consider the period feature in 650. For example, upon performing in parallel the operation 651 of confirming whether the average period is normal and the operation 652 of confirming whether the current period is normal, in the case in which the average period and the current period are all normal, the apparatus 100 for monitoring a bio-signal measuring condition may confirm whether the waveform feature is normal in 660; and in the case in which any one of the average period and the current period is abnormal, the apparatus 100 for monitoring a bio-signal measuring condition may output 'measuring condition 1' in 671. In this case, the 'measuring condition 1' may be a motion noise condition, a condition of cardiac arrhythmia, or a contact failure condition, but is not limited thereto. For example, unlike the embodiment of FIG. 6, even when the period feature is abnormal, the apparatus 100 for monitoring a bio-signal measuring condition may further consider determination on whether the waveform feature is normal; and based on the determination, the definition of 'measuring condition 1' may be modified in various manners.

Next, upon determining in 650 that the period feature is normal, the apparatus 100 for monitoring a bio-signal measuring condition may confirm a result of determination of the waveform feature in 660; and upon confirming that the waveform feature is normal, the apparatus 100 for monitoring a bio-signal measuring condition may output 'measuring condition 2' in 672, and upon confirming that the waveform feature is abnormal, the apparatus 100 for monitoring a bio-signal measuring condition may output the 'measuring condition 1' in 671. In this case, the 'measuring state 2' may be a normal measuring condition.

Figure 7:
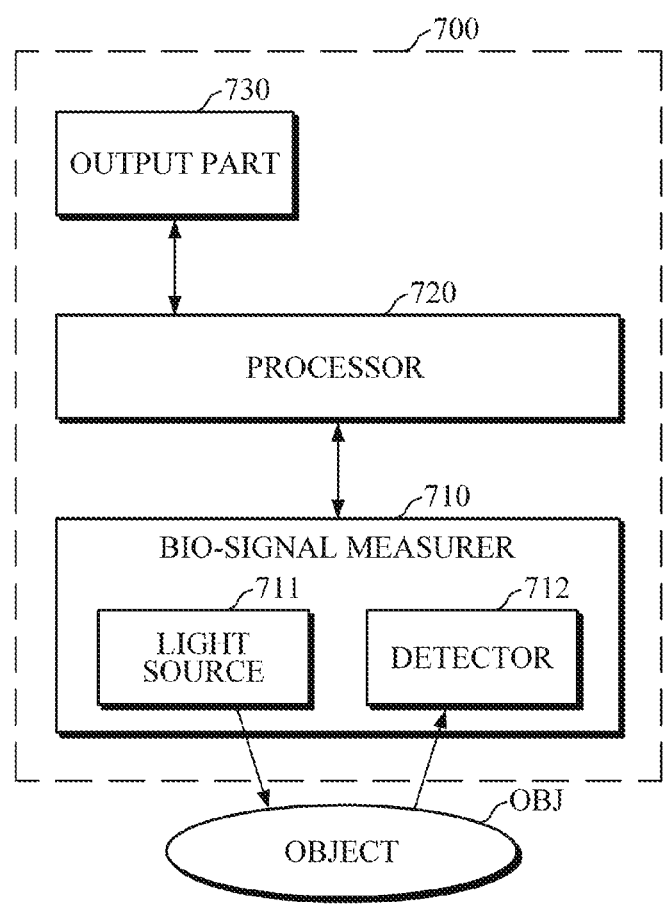
FIG. 7 is a block diagram illustrating an apparatus for measuring bio-information according to an embodiment of the disclosure.
Figure 8:
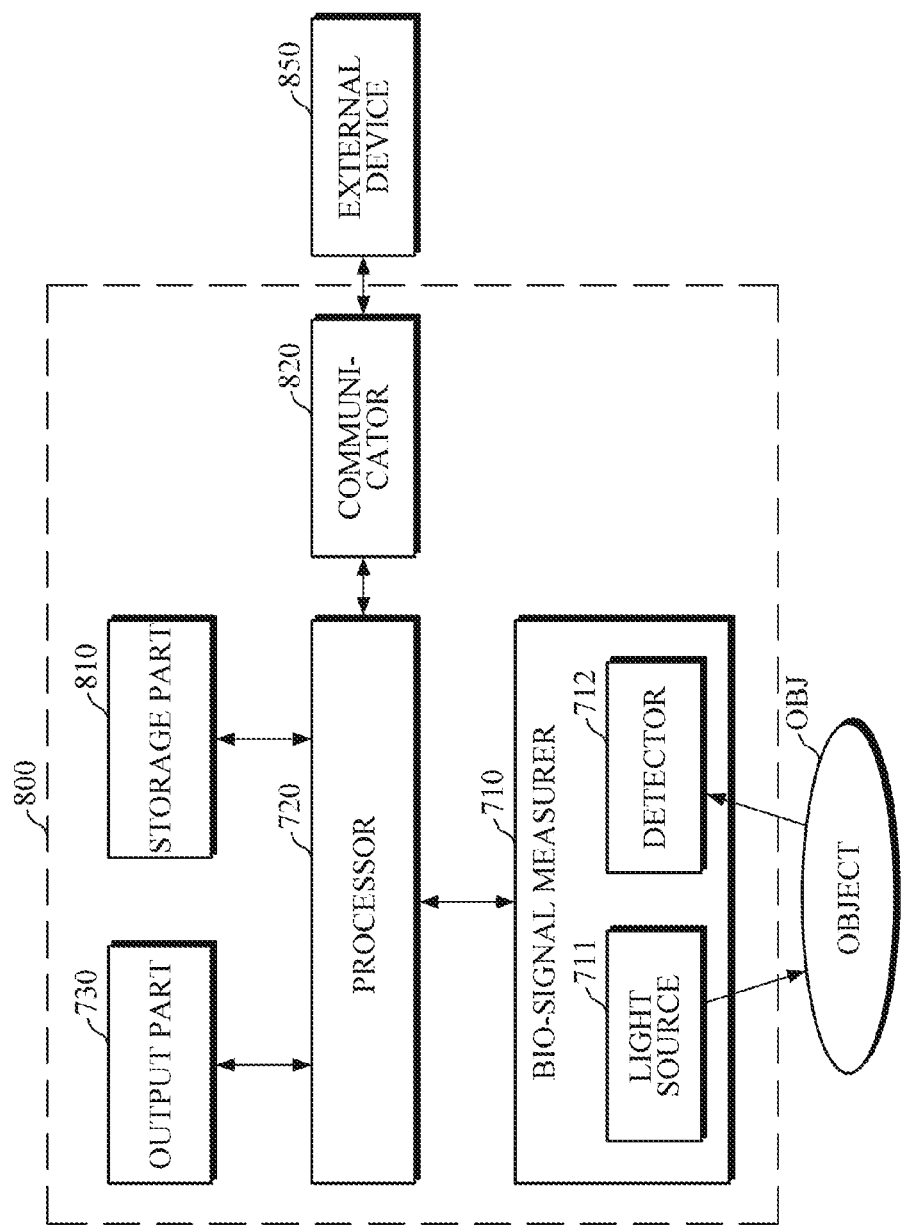
FIG. 8 is a block diagram illustrating an apparatus for measuring bio-information according to another embodiment of the disclosure.

FIG. 7 is a block diagram illustrating an apparatus for measuring bio-information according to an embodiment of the disclosure. FIG. 8 is a block diagram illustrating an apparatus for measuring bio-information according to another embodiment of the disclosure.

Apparatuses 700 and 800 for measuring bio-information of FIGS. 7 and 8 may be bio-information measuring apparatuses that measure bio-signals, such as a PPG signal and the like, from a user, and may measure bio-information, including one or more of heart rate, cardiac arrhythmia, blood pressure, vascular age, arterial stiffness, aortic pressure waveform, vascular compliance, stress index, and degree of fatigue, by using the measured bio-signals. The apparatuses 700 and 800 for measuring bio-information according to embodiments of the disclosure may include various technical aspects of monitoring the aforementioned bio-signal measuring conditions.

Referring to FIG. 7, the apparatus 700 for measuring bio-information includes a bio-signal measurer 710, a processor 720, and an output part 730.

The bio-signal measurer 710 may measure various bio-signals from an object OBJ of a user. For example, the bio-signal may be one or more of an electrocardiography (ECG) signal, a photoplethysmogram (PPG) signal, an electromyography (EMG) signal, and the like, but is not limited thereto. Hereinafter, the following description will be made using the PPG signal as an example, in which the object OBJ may be a top portion of the wrist or a finger where veins or capillaries pass. However, the object OBJ is not limited thereto, and may be a bottom portion of the wrist where the radial artery passes.

The bio-signal measurer 710 may include one or more light sources 711 that emit light onto the object, and one or more detectors 712 that detect light emitted by the one or more light sources 711 onto the object and scattered or reflected from the object.

The one or more light sources 710 may include a light emitting diode (LED), a laser diode (LD), a fluorescent body, and the like, but are not limited thereto. In the case in which a plurality of light sources are provided, each of the light sources may be configured to emit light of different wavelengths. Further, each of the light sources may be disposed at different distances from the detector 712. The one or more detectors 712 may include a photo diode, a photo transistor (PTr), an image sensor (e.g., CMOS image sensor), and the like.

The processor 720 may be electrically connected to the bio-signal measurer 710. The processor 720 may receive the bio-signal measured from the object OBJ. Further, the processor 720 may determine a measuring condition of the bio-signal, which is measured by the bio-signal measurer 710 from the object OBJ, based on the received bio-signal. In addition, the processor 720 may perform various predefined operations based on a result of determination of the bio-signal measuring condition. Various embodiments of the processor 720 will be described in further detail with reference to FIG. 9.

The output part 730 may output a processing result, e.g., the result of determination of the bio-signal measuring condition, a measurement result of bio-information, and the like, of the processor 720, by using various visual/non-visual methods. For example, the output part 730 may visually output the information on a display. For example, in the case in which the measured blood pressure value falls outside a normal blood pressure range of a user, the output part 730 may display the blood pressure value in red, or may provide a warning through vibration using a haptic module. Alternatively, the output part 730 may notify a user of the occurrence of abnormality through voice, and may provide a guide as to an action to be taken by a user. Further, the output part 730 may output the information in a non-visual manner, such as voice, tactile sensation, vibration, and the like, using a speaker module, a haptic module, and the like.

Referring to FIG. 8, the apparatus 800 for measuring bio-information includes a storage part 810 and a communicator 820 in addition to the bio-signal measurer 710, the processor 720, and the output part 730.

The storage part 810 may store various types of reference information, and a processing result of the bio-signal measurer 710 or the processor 720. In this case, the various types of reference information may include user information including a user's age, gender, health state, and the like, a linear function equation or a bio-information measuring model for measuring bio-information, determination references of each feature, e.g., an amplitude self-reference, a period general reference, a period self-reference, a waveform self-reference, and the like.

In this case, the storage part 810 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but the storage medium is not limited thereto.

The communicator 820 may communicate with an external device 850 under the control of the processor 720, to cooperate with the external device 850 in various operations associated with measurement of bio-information. In this case, examples of the external device 850 may include a smartphone, a tablet PC, a desktop computer, a laptop computer, a device of a medical institution including a cuff-type blood pressure measuring apparatus, and the like, but the external device 850 is not limited thereto.

For example, the communicator 820 may transmit a measurement result of bio-signals, a processing result of the processor 720, and the like to the external device 850, so that the external device 850 may manage a bio-information history for a user, monitor a health state of a user, output a bio-information history and a monitoring result of a health state, and the like. In another example, the communicator 820 may receive, from the external device 850, a linear function equation used for measuring bio-information, information on a bio-information measuring model, and the like. The received information may be stored in the storage part 810.

In this case, the communicator 820 may communicate with the external device 850 by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is an example and is not intended to be limiting.

Figure 9:
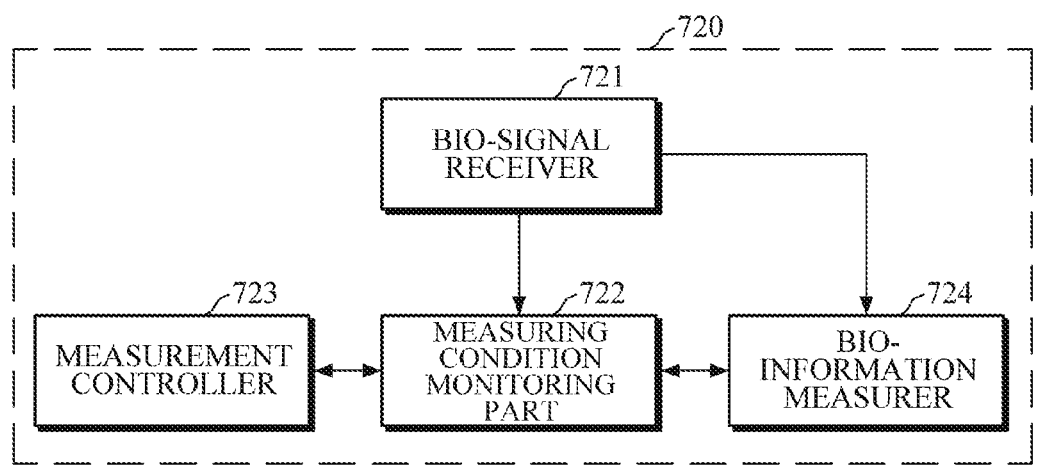
FIG. 9 is a block diagram illustrating an example of a configuration of a processor of FIGS. 7 and 8.

FIG. 9 is a block diagram illustrating an example of a configuration of a processor of FIGS. 7 and 8. Referring to FIG. 9, a processor 720 includes a bio-signal receiver 721, a measuring condition monitoring part 722, a measurement controller 723, and a bio-information measurer 724.

The bio-signal receiver 721 may receive a bio-signal from the bio-signal measurer 710. The bio-signal receiver 721 may remove noise from the bio-signal by filtering the received bio-signal as needed.

Once the bio-signal is received, the measuring condition monitoring part 722 may monitor a measuring condition of the bio-signal, measured from an object of a user, based on the received bio-signal. For example, the measuring condition monitoring part 722 may extract amplitude, period, and waveform features, and the like from the bio-signal, and may monitor a measuring condition of the bio-signal based on the extracted features. As described above, upon extracting each of the features, the measuring condition monitoring part 722 may determine whether each feature is normal by applying one or more of a general reference or a self-reference that are predetermined for each feature, may finally determine a measuring condition of the bio-signal by comprehensively considering the determination result of each feature, and may output the determination result. In this case, the output determination result of a bio-signal measuring condition may include reliability of a bio-signal measuring condition and/or a measuring condition information of a bio-signal. The measuring condition monitoring part 722 may be an example of the aforementioned apparatus 100 for monitoring a bio-signal measuring condition, which is described above in detail, such that the description thereof will be omitted.

In response to determination by the measuring condition monitoring part 722 that reliability is lower than or equal to a predetermined value, or a monitoring result of the measuring condition is not a normal measuring condition, the measuring controller 723 may control the bio-signal measurer 710 to stop measuring or to re-measure the bio-signal.

In response to determination by the measuring condition monitoring part 722 that reliability is greater than a predetermined value, or a monitoring result of the measuring condition is a normal measuring condition, the bio-information measurer 724 may measure bio-information by using the measured bio-signal. For example, the bio-information measurer 724 may measure blood pressure by applying the measured PPG signal to a pre-defined measurement model or a linear function equation.

Figure 10:
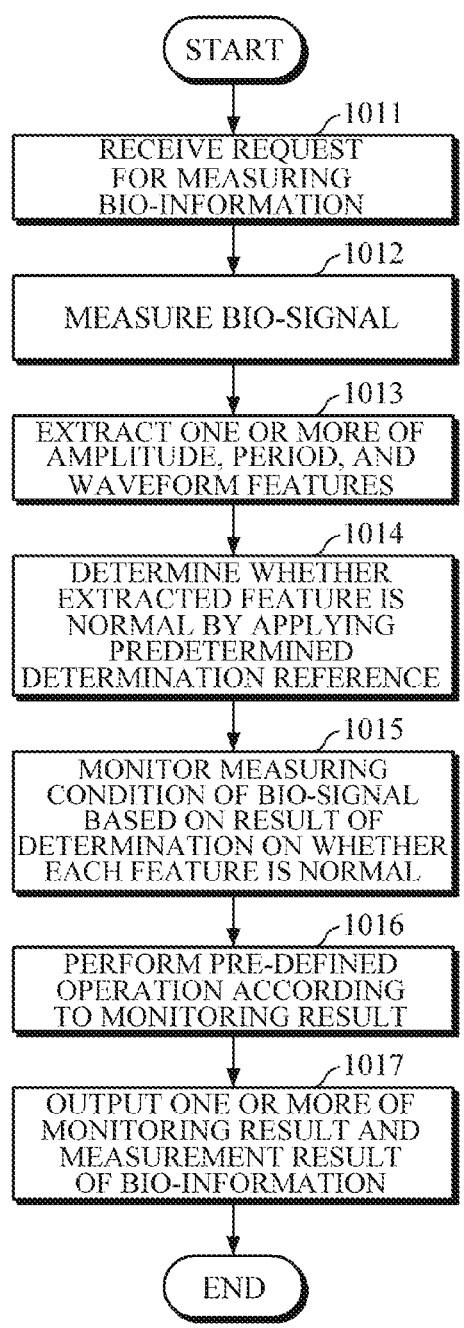
FIG. 10 is a flowchart illustrating a method for measuring bio-information according to an embodiment of the disclosure.

FIG. 10 is a flowchart illustrating a method for measuring bio-information according to an embodiment of the disclosure.

The method for measuring bio-information of FIG. 10 may be an example of a bio-information measuring method performed by the apparatuses 700 and 800 for measuring bio-information of FIGS. 7 and 8.

Referring to FIG. 10, the apparatuses 700 and 800 for measuring bio-information may receive a request for measuring bio-information in 1011. The request for measuring bio-information may be input by a user, or may be received from an external device connected through communication. However, the request for measuring bio-information is not limited thereto, and it may be determined automatically at predetermined intervals that the request for measuring bio-information is received.

Then, the apparatuses 700 and 800 for measuring bio-information may control a light source and a detector of a bio-signal measurer to measure a bio-signal from an object of a user in 1012.

Subsequently, upon measuring the bio-signal in 1012, the apparatuses 700 and 800 for measuring bio-information may extract one or more features, such as amplitude, period, and waveform features, and the like, from the measured bio-signal in 1013. In this case, the types of features to be extracted may be defined according to bio-signals, types of bio-information to be measured, and the like.

Next, the apparatuses 700 and 800 for measuring bio-information may determine whether the extracted feature is normal by applying a predetermined determination reference according to each of the features in 1014. In this case, the determination reference may be defined in various manners according to the extracted features, bio-signals, the types of bio-information, individual characteristics of a user, and the like. For example, the determination reference may be defined for each feature such as an amplitude self-reference, a period general reference, a period self-reference, and a waveform self-reference. The features may be determined in series according to a pre-defined order, but the determination is not limited thereto and the features may be determined in parallel.

Then, the apparatuses 700 and 800 for measuring bio-information may monitor a measuring condition of the bio-signal, which is measured in 1012, by comprehensively considering the results of determination on whether each feature is normal in 1015. For example, the apparatuses 700 and 800 for measuring bio-information may monitor a measuring condition by considering in parallel a result of determination on whether an amplitude, a current period, an average period, and a waveform are normal, or by considering in series the result of determination according to pre-defined priorities. The determination reference may be defined in various manners according to bio-signals, the types of bio-information, a health state of a user, individual characteristics of a user, and the like.

Subsequently, the apparatuses 700 and 800 for measuring bio-information may perform a pre-defined operation in 1016 according to a monitoring result in 1015. For example, if a monitoring result in 1015 indicates that a measuring condition of the bio-signal is normal, the apparatuses 700 and 800 for measuring bio-information may measure bio-information based on the bio-signal measured in 1012; or if not, the apparatuses 700 and 800 for measuring bio-information may stop measuring the bio-signal or may return to 1012 to re-measure the bio-signal.

Next, the apparatuses 700 and 800 for measuring bio-information may output a monitoring result, a measurement result of bio-information, and the like, and may provide the results to a user in 1017.

Figure 11:
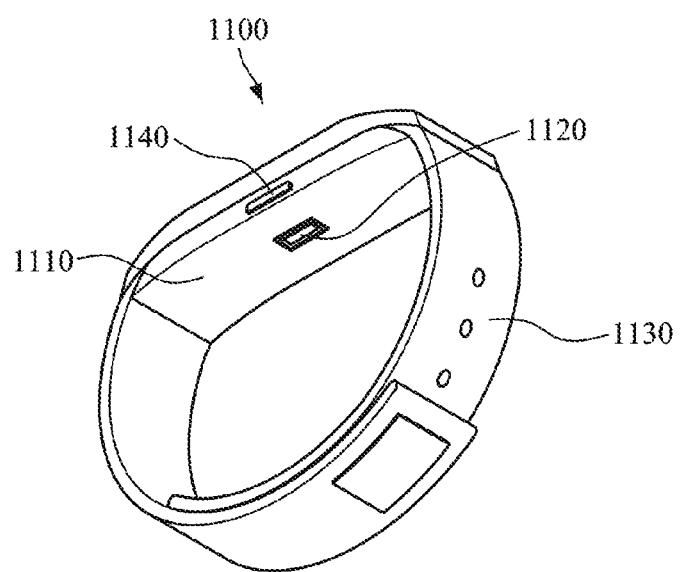
FIG. 11 is a diagram illustrating a wearable device, to which the aforementioned apparatus for measuring bio-information is applied.

FIG. 11 is a diagram illustrating a wearable device, to which the aforementioned apparatus for measuring bio-information is applied. Various embodiments of the above-described apparatuses 700 and 800 for measuring bio-information may be embedded in a smart watch worn on the wrist or a smart band-type wearable device as described therein. However, this is an example for convenience of explanation, and the types of a wearable device are not specifically limited thereto.

Referring to FIG. 11, a wearable device 1100 includes a main body 1110 and a strap 1130.

The strap 1130 may be flexible, and may be connected to both ends of the main body 1110 to be bent around a user's wrist or may be bent in a manner which allows the strap 1130 to be detached from the user's wrist. Alternatively, the strap 1130 may be formed as a band that is not detachable. In this case, air may be injected into the strap 1130 or an airbag may be included in the strap 1130, so that the strap 1130 may have elasticity according to a change in pressure applied to the wrist, and the change in pressure of the wrist may be transmitted to the main body 1110.

A battery, which supplies power to the wearable device 1100, may be embedded in the main body 1110 or the strap 1130.

Further, the wearable device 1100 includes a bio-signal measurer 1120, which measures a pulse wave signal and a contact pressure signal from an object, and a processor that monitors a measuring condition of the bio-signal by using the bio-signal measured by the bio-signal measurer 1120, and measures bio-information of a user based on the monitoring result.

The bio-signal measurer 1120 may include a PPG sensor that is mounted to be exposed to a bottom portion of the main body 1110, i.e., a portion that comes into contact with an object (e.g., wrist of a user), to measure a bio-signal from the object. In addition, the bio-signal measurer 1120 may further include a contact pressure sensor that is mounted inside the main body 1110 to measure a contact pressure signal between the PPG sensor and the object.

The PPG sensor may include one or more light sources, which emit light onto the object, and one or more detectors that detect light emitted from the object; and may measure a plurality of PPG signals of different wavelengths from the object.

In response to a request for measuring bio-information of a user, the processor may generate a control signal to control the bio-signal measurer 1120, and may measure bio-information, such as blood pressure, by using the PPG signal and/or the contact pressure signal that are measured by the bio-signal measurer 1120.

Once the bio-signal measurer 1120 measures the bio-signal from a user, the processor may monitor a measuring condition of the bio-signal by using the measured bio-signal. In this case, the processor may extract amplitude, period, and waveform features from the measured bio-signal, and may monitor the measuring condition of the bio-signal by using various pre-defined determination references, which is described above in detail, such that the description thereof will be omitted.

A display may be mounted on a front surface of the main body 1110, and may visually output a monitoring result of a bio-signal measuring condition and/or a measuring result of bio-information.

Based on the monitoring result of the bio-signal measuring condition that is displayed on the display, a user may adjust pressure, a contact state, and the like between the bio-signal measurer 1120 and the object, and control the bio-signal measurer 1120 to re-measure the bio-signal.

The wearable device 110 may further include a manipulator 1140 that receives a control instruction of a user and transmits the received control instruction to the processor. The manipulator 1140 may be mounted on the side of the main body 1110, and may include a function to input a instruction to turn on/off the wearable device 1100.

In addition, the wearable device 1100 may include a communicator to transmit and receive various data to and from an external device, and various other modules for performing additional functions provided by the wearable device 1100.

Figure 12:
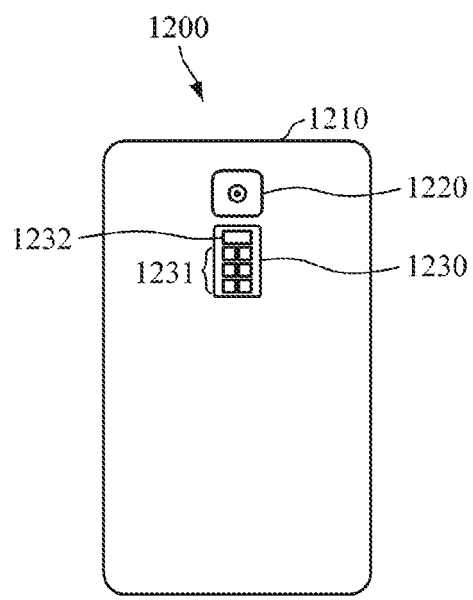
FIG. 12 is a diagram illustrating a smart device, to which the aforementioned apparatus for measuring bio-information is applied.

FIG. 12 is a diagram illustrating a smart device, to which the aforementioned apparatus for measuring bio-information is applied. As described above, various embodiments of the above-described apparatuses 700 and 800 for measuring bio-information may be applied to a smart device such as a smart phone, a tablet PC, and the like.

Referring to FIG. 12, a smart device 1200 may be mounted on a rear surface of a main body 1210 so that a bio-signal measurer 1230 may be exposed to the outside. In this case, the bio-signal measurer 1230 may include one or more light sources 1231 and one or more detectors 1232. Each of the light sources 1231 may include a light emitting diode (LED), and the like, and at least some of the light sources 1231 may be configured to emit light of different wavelengths. The detector 1232 may include a photo diode, a photo transistor, and the like.

Further, a display may be mounted on a front surface of the main body 1210. The display may visually display a monitoring result of a bio-signal measuring condition, a measuring result of bio-information, and the like.

In addition, an image sensor 1220 may be mounted at the main body 1210. When an object (e.g., finger) of a user approaches the bio-signal measurer 1230 to measure a bio-signal, the image sensor 1220 may capture an image of the finger and transmit the captured image to the processor. In this case, based on the image of the finger, the processor may identify a relative position of the finger with respect to an actual position of the bio-signal measurer 1230, and may provide the relative position of the finger to the user through the display, thereby providing a guide for measuring the bio-signal more accurately.

Various other modules for performing many functions of the aforementioned apparatus for measuring bio-information may be mounted in the smart device 1220, detailed description of which will be omitted.

Embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments for realizing embodiments can be easily deduced by one of ordinary skill in the art.

Embodiments have been described herein. However, it will be obvious to those skilled in the art that various changes and modifications can be made without changing technical ideas and features of the disclosure. Thus, it is clear that the above-described embodiments are illustrative in all aspects and are not intended to limit the disclosure.

What is claimed is:

1. An apparatus for monitoring a bio-signal measuring condition, the apparatus comprising:
   a bio-signal receiver configured to receive a bio-signal measured by a bio-signal measurement device, the bio-signal being measured from a user; and
   a processor configured to:
      extract any one or any combination of a waveform feature, a period feature, and an amplitude feature, from the received bio-signal;
      determine whether each of the extracted any one or any combination of the waveform feature, the period feature, and the amplitude feature correspond to one of a first state and a second state, using at least one predetermined determination reference corresponding to the extracted any one or any combination of the waveform feature, the period feature, and the amplitude features;
      monitor a measuring condition of the received bio-signal, in response to a determination that all of the extracted any one or any combination of the waveform feature, the period feature, and the amplitude feature correspond to the first state; and
      control the apparatus to provide an output indicating that a measuring problem is occurring with the bio-signal measurement device, in response to a determination that one of the extracted period feature, the extracted waveform feature, and amplitude feature correspond to the second state,
   wherein the extracted period feature comprises a current period of the received bio-signal and an average period of the received bio-signal during a predetermined period of time, and
   wherein the processor is further configured to:
      determine whether the current period corresponds to the first state using a period self-reference that is individualized for the user, and
      determine whether the average period corresponds to the first state using a period general reference for bio-information to be measured using the bio-signal.

2. The apparatus of claim 1, wherein the processor is further configured to determine whether the extracted waveform feature corresponds to the first state, using a waveform self-reference that is individualized for the user.

3. The apparatus of claim 2, wherein the waveform self-reference comprises any one or any combination of a reference time interval, a number of comparison samples, an order of differentiation, and a failure condition.

4. The apparatus of claim 3, wherein the processor is further configured to:
   extract a waveform of a current time interval, from the received bio-signal;
   obtain a first waveform and a second waveform, from the extracted waveform of the current time interval and a waveform of the reference time interval, based on the order of differentiation;
   compare the obtained first waveform and the obtained second waveform; and
   based on a result of the obtained first waveform being compared with the obtained second waveform satisfying the failure condition, determine that the extracted waveform feature corresponds to the second state.

5. The apparatus of claim 4, wherein the processor further comprises a buffer configured to store data of the waveform of the reference time interval of the bio-signal.

6. The apparatus of claim 5, wherein the processor is further configured to, based on the waveform of the current time interval satisfying a predetermined update reference, update the stored data of the waveform of the reference time interval, using data of the waveform of the current time interval.

7. The apparatus of claim 4, wherein the failure condition comprises any one or any combination of a minimum threshold of similarity between waveforms, a number of times of successive failures to reach the minimum threshold, a start point of a similarity comparison between waveforms, and a total beat count for calculating an average similarity value.

8. The apparatus of claim 7, wherein the processor is further configured to:
   calculate a similarity between the obtained first waveform and the obtained second waveform; and
   based on the calculated similarity being lower than the minimum threshold, determine that the extracted waveform feature corresponds to the second state.

9. The apparatus of claim 8, wherein the processor is further configured to, based on the calculated similarity between the obtained first waveform and the obtained second waveform being lower than the minimum threshold, and the number of times of the successive failures to reach the minimum threshold satisfying a predetermined number of times, determine that the extracted waveform feature corresponds to the second state.

10. The apparatus of claim 8, wherein the similarity between the waveforms comprises any one or any combination of a correlation coefficient, an average value, and a sum total of comparison samples of the first waveform and the second waveform.

11. The apparatus of claim 1, wherein the processor is further configured to determine whether the extracted amplitude feature corresponds to the first state, using an amplitude self-reference that is individualized for the user.

12. The apparatus of claim 1, wherein the processor is further configured to output either one or both of a reliability of the measuring condition of the bio-signal and information of the measuring condition, based on whether the extracted any one or any combination of the waveform feature, the period feature, and the amplitude feature are determined to correspond to the first state according to predetermined priorities of each of the extracted any one or any combination of the waveform feature, the period feature, and the amplitude feature.

13. The apparatus of claim 12, wherein the predetermined priorities are determined based on any one or any combination of an examination position, types of bio-signals, types of bio-information to be measured, and a computing performance of a bio-information measuring apparatus.

14. The apparatus of claim 12, wherein the processor is further configured to:
based on the extracted amplitude feature being determined to correspond to the first state, while the extracted period feature and the extracted waveform feature are determined to correspond to a second state, determine the measuring condition to be a motion noise condition;
based on the extracted period feature being determined to correspond to the first state, while the extracted amplitude feature and the extracted waveform feature are determined to correspond to a second state, determine the measuring condition to be an ambient light noise condition;
based on the extracted waveform feature being determined to correspond to the first state, while the extracted period feature and the extracted amplitude feature are determined to correspond to a second state, determine the measuring condition to be a condition of not measuring the bio-signal;
based on the extracted period feature being determined to correspond to a second state, while the extracted amplitude feature and the extracted waveform feature are determined to correspond to the first state, determine the measuring condition to be a condition of cardiac arrhythmia;
based on the extracted amplitude feature being determined to correspond to a second state, while the extracted period feature and the extracted waveform feature are determined to correspond to the first state, determine the measuring condition to be an inadequate contact pressure condition;
based on the extracted waveform feature being determined to corresponds to a second state, while the extracted period feature and the extracted amplitude feature are determined to correspond to the first state, determine the measuring condition to be a contact failure condition; and
based on the extracted period feature, the extracted amplitude feature, and the extracted waveform features being determined to correspond to the first state, determine the measuring condition to be a measuring condition of the first state.

15. A method for monitoring a bio-signal measuring condition, the method comprising:
receiving a bio-signal measured by a bio-signal measurement device, the bio-signal being measured from a user;
extracting any one or any combination of a waveform feature, a period feature, and an amplitude feature, from the received bio-signal;
determining whether each of the extracted any one or any combination of the waveform feature, the period feature, and the amplitude feature correspond to one of first state and a second state, using a predetermined determination reference corresponding to the extracted any one or any combination of the waveform feature, the period feature, and the amplitude features; and
monitoring a measuring condition of the received bio-signal, in response to a determination that all of the extracted any one or any combination of the waveform feature, the period feature, and the amplitude feature correspond to the first state; and
control an apparatus to provide an output indicating that a measuring problem is occurring with the bio-signal measurement device, in response to a determination that one of the extracted period feature, the extracted waveform feature, and amplitude feature correspond to the second state,
wherein the extracted period feature comprises a current period of the received bio-signal and an average period of the received bio-signal during a predetermined period of time, and
wherein the determining whether each of the extracted any one or any combination of the waveform feature, the period feature, and the amplitude feature correspond to one of a first state and a second state comprises:
determining whether the current period corresponds to the first state using a period self-reference that is individualized for the user, and
determining whether the average period corresponds to the first state using a period general reference that is individualized for bio-information to be measured using the bio-signal.

16. The method of claim 15, wherein the determining whether the extracted any one or any combination of the waveform feature, the period feature, and the amplitude feature correspond to the first state comprises determining whether the extracted waveform feature corresponds to the first state, using a waveform self-reference that is individualized for the user.

17. The method of claim 16, wherein the determining whether the extracted waveform feature correspond to the first state comprises:
extracting a waveform of a current time interval, from the received bio-signal;
obtaining a first waveform and a second waveform, from the extracted waveform of the current time interval and a waveform of a reference time interval, based on an order of differentiation;
comparing the obtained first waveform and the obtained second waveform; and
based on a result of the obtained first waveform being compared with the obtained second waveform satisfying a failure condition, determining that the extracted waveform feature corresponds to a second state.

18. The method of claim 17, wherein the comparing the obtained first waveform and the obtained second waveform comprises calculating a similarity between the obtained first waveform and the obtained second waveform, and wherein the determining that the extracted waveform feature corresponds to a second state comprises, based on the calculated similarity being lower than a minimum threshold of similarity between waveforms, determining that the extracted waveform feature corresponds to a second state.

19. The method of claim 15, wherein the determining whether the extracted any one or any combination of the waveform feature, the period feature, and the amplitude feature correspond to the first state comprises determining whether the extracted amplitude feature corresponds to the first state, using an amplitude self-reference that is individualized for the user.

20. The method of claim 15, wherein the monitoring the measuring condition of the received bio-signal comprises outputting either one or both of a reliability of the measuring condition of the bio-signal and information of the measuring condition, based on whether the extracted any one or any combination of the waveform feature, the period feature, and the amplitude feature are determined to correspond to the first state according to predetermined priorities of each of the extracted any one or any combination of the waveform feature, the period feature, and the amplitude feature.

21. An apparatus for measuring bio-information, the apparatus comprising:
a bio-signal measurer configured to measure a bio-signal by emitting a first light onto an object and receiving a second light that is reflected from the object onto which the first light is emitted;
a processor configured to:
extract one or more features, from the measured bio-signal;
monitor a measuring condition of the measured bio-signal, using at least one predetermined determination reference corresponding to the extracted one or more features; and
determine whether each of the extracted one or more features correspond to one of a first state and a second state, using either one or both of a self-reference and a general reference that are included in the at least one predetermined determination reference;
output information of the measuring condition, in response to a determination that all of the extracted one or more features correspond to the first state; and
output information of indicating that a measuring problem is occurring with the bio-signal measurer, in response to a determination that one of the extracted one or more features correspond to the second state; and
an output part configured to output a processing result of the processor, on a display,
wherein the extracted one or more features comprises a period feature comprising a current period of the received bio-signal and an average period of the received bio-signal during a predetermined period of time, and
wherein the processor is further configured to:
determine whether the current period corresponds to the first state using a period self-reference that is individualized for the user, and
determine whether the average period corresponds to the first state using a period general reference for bio-information to be measured using the bio-signal.

22. The apparatus of claim 21, wherein the bio-signal measurer comprises:
one or more light sources configured to emit the first light onto the object; and
one or more detectors configured to receive the second light reflected from the object.

23. The apparatus of claim 21, wherein the processor is further configured to:
control the bio-signal measurer to stop and start the measuring of the bio-signal, based on the output information of the measuring condition; and
measure bio-information, using the measured bio-signal, based on the output information of the measuring condition.

24. The apparatus of claim 23, wherein the bio-information comprises any one or any combination of a heart rate, a cardiac arrhythmia, a blood pressure, a vascular age, an arterial stiffness, an aortic pressure waveform, a vascular compliance, a stress index, and a degree of fatigue.

25. The apparatus of claim 23, further comprising a storage part configured to store any one or any combination of the at least one predetermined determination reference, the measured bio-signal, information on whether each of the extracted one or more features is determined to correspond to the first state, the monitored measuring condition, and the measured bio-information.

26. The apparatus of claim 23, further comprising a communicator configured to transmit and receive, to and from an external device, the at least one predetermined determination reference, the measured bio-signal, information on whether each of the extracted one or more features is determined to correspond to the first state, the monitored measuring condition, and the measured bio-information.

27. A method for measuring bio-information, the method comprising:
measuring a bio-signal using a bio-signal measurement device, by emitting a first light onto an object and receiving a second light that is reflected from the object on to which the first light is emitted;
extracting one or more features, from the measured bio-signal;
monitoring a measuring condition of the measured bio-signal, using at least one predetermined determination reference corresponding to the extracted one or more features;
determining whether each of the extracted one or more features correspond to one of a first state and a second state, using either one or both of a self-reference and a general reference that are included in the at least one predetermined determination reference;
outputting information of the measuring condition, in response to a determination that all of the extracted one or more features correspond to the first state;
outputting information indicating that a measuring problem is occurring with the bio-signal measurement device, in response to a determination that one of the extracted one or more features correspond to the second state, the output information being a non-visual indicator; and
performing a pre-defined operation, based on the monitored measuring condition,
wherein the extracted one or more features comprises a period feature comprising a current period of the received bio-signal and an average period of the received bio-signal during a predetermined period of time, and wherein determining whether each of the extracted one or more features correspond to one of a first state and a second state comprises:
  determining whether the current period corresponds to the first state using a period self-reference that is individualized for the user, and
  determining whether the average period corresponds to the first state using a period general reference that is individualized for bio-information to be measured using the bio-signal.

28. The method of claim 27, wherein the monitoring the measuring condition of the bio-signal comprises:
  based on determining that the extracted one or more features correspond to the second state, information indicating that a measuring problem is occurring comprising any one or any combination of a motion noise condition, an ambient light noise condition, a condition of not measuring the bio-signal, a condition of cardiac arrhythmia, an inadequate contact pressure condition, a contact failure condition, and a normal measuring condition.

29. The method of claim 28, wherein the performing the pre-defined operation comprises, based on the output information of the measuring condition, controlling to stop and start the measuring of the bio-signal, and measuring bio-information, using the measured bio-signal.

30. The method of claim 29, further comprising outputting a result of the measuring the bio-information.

31. An apparatus for monitoring a bio-signal measuring condition, the apparatus comprising:
  a bio-signal receiver configured to receive a bio-signal measured by a bio-signal measurement device, the bio-signal being measured from a user; and
  a processor configured to:
    extract a waveform, a current period, an average period and an amplitude, from the received bio-signal;
    determine whether the extracted waveform corresponds to one of the first state or a second state by comparing the extracted waveform to a reference waveform;
    determine whether the extracted amplitude correspond to the first state by comparing the extracted amplitude to a reference amplitude;
    determine whether the extracted period correspond to the first state by comparing the extracted period to a reference period based on a period self-reference that is individualized for the user;
    determine whether the average period corresponds to the first state using a period general reference for bio-information to be measured using the bio-signal;
    based on the extracted amplitude being determined to correspond to a second state, control the apparatus to provide an output indicating any one or any combination of an inadequate contact pressure condition of the bio-signal measurement device, an ambient light noise condition of the bio-signal measurement device, and a condition of not measuring the bio-signal of the bio-signal measurement device;
    based on one of the extracted period and the extracted waveform being determined to correspond to a second state, control the apparatus to provide an output indicating any one or any combination of a motion noise condition of the bio-signal measurement device, a condition of cardiac arrhythmia detected by the bio-signal measurement device, and a contact failure condition of the bio-signal measurement device; and
    based on the extracted amplitude, the extracted period, and the extracted waveform being determined to correspond to the first state, control the apparatus to indicate a normal measuring condition of the bio-signal measurement device.

32. The apparatus of claim 31, wherein the determining whether the extracted waveform corresponds to the first state comprises determining that the extracted waveform corresponds to the first state, based on a similarity of the extracted waveform and the reference waveform being greater than a threshold,
  wherein the determining whether the extracted amplitude corresponds to the first state comprises determining that the extracted amplitude corresponds to the first state, based on a first difference between the extracted amplitude and the reference amplitude being within a first range, and
  wherein the determining whether the extracted period corresponds to the first state comprises determining that the extracted period corresponds to the first state, based on a second difference between the extracted period and the reference period being within a second range.

* * * * *